United States Patent
Shimokawa et al.

(10) Patent No.: US 10,413,756 B2
(45) Date of Patent: Sep. 17, 2019

(54) ULTRASOUND TREATMENT DEVICE AND CONTROL METHOD THEREOF

(75) Inventors: Hiroaki Shimokawa, Sendai (JP); Hiroshi Kanai, Sendai (JP); Takashi Mochiduki, Mitaka (JP); Yoshinori Seki, Mitaka (JP)

(73) Assignees: Hitachi, Ltd., Tokyo (JP); TOHOKU UNIVERSITY, Sendai-shi (JP)

( * ) Notice: Subject to any disclaimer, the term of this patent is extended or adjusted under 35 U.S.C. 154(b) by 1205 days.

(21) Appl. No.: 13/990,233

(22) PCT Filed: Dec. 9, 2010

(86) PCT No.: PCT/JP2010/072171
§ 371 (c)(1),
(2), (4) Date: May 29, 2013

(87) PCT Pub. No.: WO2012/077219
PCT Pub. Date: Jun. 14, 2012

(65) Prior Publication Data
US 2013/0261508 A1    Oct. 3, 2013

(51) Int. Cl.
*A61N 7/00*    (2006.01)
*A61B 8/00*    (2006.01)
(Continued)

(52) U.S. Cl.
CPC ............. *A61N 7/00* (2013.01); *A61B 8/085* (2013.01); *A61B 8/5276* (2013.01); *A61N 7/02* (2013.01);
(Continued)

(58) Field of Classification Search
CPC ......... A61B 8/40; A61B 8/5276; A61B 8/085; A61N 7/00; A61N 2007/0082; A61N 7/02
See application file for complete search history.

(56) References Cited

U.S. PATENT DOCUMENTS 5,080,101 A * 1/1992 Dory .................. A61B 8/08
600/439
8,099,154 B1 1/2012 Wess et al.
(Continued)

FOREIGN PATENT DOCUMENTS

CN    1487845 A    4/2004
CN    1968656 A    5/2007
(Continued)

OTHER PUBLICATIONS

Chinese Office Action dated Jan. 27, 2015, issued in corresponding CN Patent Application No. 201080070638.2 with English translation (19 pages).
(Continued)

*Primary Examiner* — Amanda Lauritzen Moher
(74) *Attorney, Agent, or Firm* — Westerman, Hattori, Daniels & Adrian, LLP (57) ABSTRACT

When a user designates a treatment range on a diagnostic image, a switch (12) selects a transmitter for treatment (16). Ultrasound with intensity for treatment is thereby transmitted from a probe (10) to the inside of an organism. When the treatment operation continues for a prescribed time, a control unit (18) controls the switch (12) to select a transmitter for diagnosis (14). The probe (10) thereby emits an ultrasound beam for diagnosis, senses an echo thereof, generates a diagnostic image, and carries out an inspection of a positional shift of the site to be treated. In the inspection, the control unit (18) compares the diagnostic image with a reference image, and if a significant difference is detected therebetween, determines that a shift has occurred, issues an alarm, and urges the user to correct the positional shift. It is possible to resume the treatment when the positional shift has been corrected.

17 Claims, 8 Drawing Sheets

(51) Int. Cl.
   *A61B 8/08* (2006.01)
   *A61N 7/02* (2006.01)
(52) U.S. Cl.
   CPC ......... *A61B 8/40* (2013.01); *A61N 2007/0082* (2013.01)

(56) References Cited

U.S. PATENT DOCUMENTS

| | | | |
|---|---|---|---|
| 2003/0163045 | A1 | 8/2003 | Gatzke |
| 2004/0059219 | A1 | 3/2004 | Asafusa |
| 2005/0080468 | A1 | 4/2005 | Christman |
| 2005/0261584 | A1* | 11/2005 | Eshel ............. A61B 8/00 600/439 |
| 2006/0074355 | A1 | 4/2006 | Slayton et al. |
| 2008/0269607 | A1 | 10/2008 | Ishida et al. |
| 2009/0088623 | A1* | 4/2009 | Vortman ............ A61B 5/416 600/411 |
| 2009/0216159 | A1 | 8/2009 | Slayton et al. |
| 2010/0056918 | A1 | 3/2010 | Sato et al. |
| 2010/0222676 | A1* | 9/2010 | Ogihara ............ A61B 8/13 600/439 |
| 2010/0266099 | A1* | 10/2010 | Busch ............. A61N 5/1048 378/65 |
| 2012/0209118 | A1* | 8/2012 | Warnking ........... A61B 8/085 600/439 |

FOREIGN PATENT DOCUMENTS

| | | |
|---|---|---|
| CN | 101658432 A | 3/2010 |
| EP | 1757244 A1 | 2/2007 |
| JP | 62-047358 A | 3/1987 |
| JP | 09-103434 A | 4/1997 |
| JP | 3058645 B2 | 7/2000 |
| JP | 2000-229098 A | 8/2000 |
| JP | 2000-237205 A | 9/2000 |
| JP | 2004-290548 A | 10/2004 |
| JP | 2005-304918 A | 11/2005 |
| JP | 3742771 B2 | 2/2006 |
| JP | 2007-089927 A | 4/2007 |
| JP | 2007-185249 A | 7/2007 |
| JP | 2008-514294 A | 5/2008 |
| JP | 2008-132109 A | 6/2008 |
| WO | 2004/075977 A2 | 9/2004 |
| WO | 2005/120373 A1 | 12/2005 |

OTHER PUBLICATIONS

Japanese Office Action dated Dec. 3, 2013, issued in Japanese Patent Application No. 2009-160862, w/English translation (4 pages).
International Search Report for PCT/JP2010/072171, dated Feb. 1, 2011.
Extended (supplementary) European Search Report dated Feb. 9, 2017, issued in counterpart application No. 10860405.9 (10 pages).
Notification of Transmittal of Translation of the International Preliminary Report on Patentability (Forms PCT/IB/338) of International application No. PCT/JP2010/072171 dated Jun. 20, 2013 with forms PCT/IB/326, PCT/IB373 and PCT/ISA/237, (15 pages).
Japanese Office Action dated Jul. 23, 2013, issued in corresponding Japanese Patent Application No. 2009-160862, w/English translation.
Office Action dated Feb. 5, 2018, issued in European application No. 10860405.9. (7 pages).

* cited by examiner

ULTRASOUND TREATMENT DEVICE AND CONTROL METHOD THEREOF

TECHNICAL FIELD

The present invention relates to an ultrasound treatment device and to a method for controlling an ultrasound treatment device.

BACKGROUND ART

As treatment for an ischemic tissue, such as treatment for myocardial infarction, for example, invasive treatment by surgery has been conventionally performed. This method is highly invasive to and imposes a significant burden on patients.

In order to address the above problem, a method for performing treatment by using shockwaves has been developed. In this therapy, cardiac muscle tissues which are damaged due to narrowing or obstruction of a part of the coronary artery of heart are irradiated with weak shockwaves for treatment. It is known that irradiation of an ischemic tissue with shockwaves would provide a therapeutic effect for accelerating regeneration of new blood vessels. This therapy is noninvasive and therefore imposes less burden on patients. As an example device for use with such a therapy, a device which is described in Patent Document 1 has been known. This device is an application of a lithotripsy device in which an affected area is irradiated with shockwaves whose output has been weakened compared to the output of a lithotripsy device.

In this type of device, as it is not possible to obtain an image within a living organism by a shockwave irradiation head, it is necessary to further provide a separate ultrasound diagnosis device for specifying a portion to be irradiated and so on. Further, as it is not possible to place the ultrasound diagnosis probe at the same position as the shockwave irradiation head, a diagnosis image is captured by the ultrasound diagnosis device from a visual point and in a line of sight that are different from those of the shockwave irradiation head.

Meanwhile, Patent Document 2 discloses a device which irradiates a wound area caused by bone fracture, decubitus bedscore, or the like, with ultrasound pulses, to thereby facilitate angiogenesis.

Further, Patent Document 3 discloses a system which performs treatment and imaging processing with a single transducer (see particularly paragraphs 0044 and 0045 and FIGS. 7A and 7B). While this apparatus is mainly aimed at treatment of a superficial tissue for cosmetic purposes, angiogenesis is described as one of the therapy effects (see particularly paragraphs 0013 and 0026).

Also, Patent Document 4 discloses an apparatus which stimulates a portion suffering from myocardial infarction, a fractured portion, a portion of orthodontic treatment, or the like, with ultrasound irradiation intensively for a predetermined time period, thereby achieving therapy effects. In this apparatus, a single transducer is caused to perform irradiation of stimulating pulse waves and irradiation of ultrasound observation pulse waves in a switchable manner, thereby enabling follow-up of the irradiated portion.

PRIOR ART DOCUMENTS

Patent Literature

Patent Document 1: JP 3058645 B
Patent Document 2: JP 2005-304918 A
Patent Document 3: JP 2008-514294 A
Patent Document 4: JP 62-47358 A

DISCLOSURE OF THE INVENTION

Technical Problems

In treatment which promotes angiogenesis and revascularization by ultrasound stimulus, it is necessary to apply irradiation of ultrasound to an affected area for a relatively long time (for several tens of minutes to several hours, for example). While it is necessary to fix the patient's posture during that time period for treatment in order to apply the irradiation of ultrasound correctly to a target portion to be treated, in practice it is difficult to keep the patient's posture fixed for such a long time period. Therefore, measures are required for minimizing the irradiation of ultrasound applied to portions other than the treatment target portion.

Solution to Problems

In one aspect of the present invention, there is provided an ultrasound treatment device, including a diagnosis ultrasound transmitter for transmitting ultrasound with intensity for diagnosis; a treatment ultrasound transmitter for transmitting ultrasound with intensity for treatment which is stronger than the intensity for diagnosis, from a transmission position which is substantially the same as a transmission position of the diagnosis ultrasound transmitter; a sequence controller that causes the treatment ultrasound transmitter to transmit the ultrasound with intensity for treatment during a treatment period and also causes the diagnosis ultrasound transmitter to transmit the ultrasound with intensity for diagnosis at each inspection timing that satisfies a predetermined condition, thereby generating a diagnosis image at the inspection timing; a shift detection unit that detects a positional shift of a treatment target portion, based on comparison between a diagnostic image generated at a certain inspection timing and a diagnostic image which has been generated at an inspection timing prior to the certain inspection timing and stored; and a shift correction processing unit that performs predetermined shift correction processing when a positional shift of the treatment target portion is detected by the shift detection unit.

In a certain mode, the ultrasound treatment device further includes a display controller that, before the start of the treatment period in which the treatment ultrasound transmitter is used, causes the diagnosis ultrasound transmitter to transmit the ultrasound with intensity for diagnosis to thereby generate a diagnostic image for treatment range designation and display the diagnostic image that is generated on a display device; a range designation receiving unit that receives from a user designation of a treatment range with respect to the diagnostic image for treatment range designation displayed on the display device; and a treatment controller that controls the treatment ultrasound transmitter to transmit the ultrasound with intensity for treatment to the treatment range that is received by the range designation receiving unit.

In a further mode, the treatment ultrasound transmitter is capable of transmitting an ultrasound beam as the ultrasound with intensity for treatment, while varying a scanning position and a focus depth of the beam, and the treatment controller causes the treatment ultrasound transmitter to transmit the ultrasound beam while varying the scanning position and the focus depth of the beam within the treatment range in accordance with a predetermined treatment plan pattern.

In a different mode, the ultrasound treatment device further includes a treatment time accumulation unit that accumulates a time period in which the treatment ultrasound transmitter transmits the ultrasound with intensity for treatment from a start point which is a starting time point of the treatment period, and, when a positional shift of the treatment target portion is detected by the shift detection unit, the shift correction processing unit causes the treatment time accumulation unit to interrupt accumulation until the resumption of subsequent treatment by the treatment ultrasound transmitter, and when treatment by the treatment ultrasound transmitter is resumed subsequently, controls the treatment time accumulation unit to resume accumulation from an accumulated value corresponding to a time point at which the positional shift was detected.

In a further mode, the ultrasound treatment device further includes a treatment progress recording unit that records, at each inspection timing, a diagnostic image generated at the inspection timing in association with a value of the irradiation time duration in the treatment time accumulation unit at the inspection timing.

In another mode, the ultrasound treatment device further includes a vital signal detection unit that detects a vital signal corresponding to a periodical movement of a living organism to be treated, and the sequence controller selects, as the inspection timing that satisfies a predetermined condition, a timing point at which a time phase of a movement of the living organism which is obtained from the vital signal detected by the vital signal detection unit corresponds to a predetermined time phase, the time point being near a time point at which a predetermined unit treatment time has elapsed from the previous inspection timing.

In still another mode, the sequence controller causes the treatment ultrasound transmitter to stop transmitting the ultrasound with intensity for treatment while a diagnostic image at the inspection timing is being generated by the diagnosis ultrasound transmitter.

In a further mode, the ultrasound treatment device further includes a forced switching instruction unit that receives, when the ultrasound with intensity for treatment is being transmitted from the treatment ultrasound transmitter under the control of the sequence controller, an instruction from the user to perform an operation to stop the transmission of the transmission ultrasound and cause the diagnosis ultrasound transmitter to transmit the ultrasound with intensity for diagnosis to thereby generate a diagnostic image.

In another aspect of the present invention, there is provided a method for controlling an ultrasound treatment device including a diagnosis ultrasound transmitter for transmitting ultrasound with intensity for diagnosis; and a treatment ultrasound transmitter for transmitting ultrasound with intensity for treatment which is stronger than the intensity for diagnosis. This control method includes causing the treatment ultrasound transmitter to transmit the ultrasound with intensity for treatment from a predetermined transmission position during a treatment period; causing the diagnosis ultrasound transmitter to transmit the ultrasound with intensity for diagnosis from a transmission position which is substantially the same as the transmission position at each inspection timing that satisfies a predetermined condition, thereby generating a diagnosis image at the inspection timing; detecting a positional shift of a treatment target portion, based on comparison between a diagnostic image generated at a certain inspection timing and a diagnostic image which has been generated at an inspection timing prior to the certain inspection timing and stored; and performing predetermined shift correction processing when a positional shift of the treatment target portion is detected.

Advantageous Effects of Invention

According to the present invention, it is possible to confirm whether or not a treatment target portion has been shifted, by generating a diagnosis image and comparing the diagnostic image with a previous image at each inspection timing, and to perform shift correction processing for correcting the shift when a shift has occurred.

MODE FOR CARRYING OUT THE INVENTION

Figure 1:
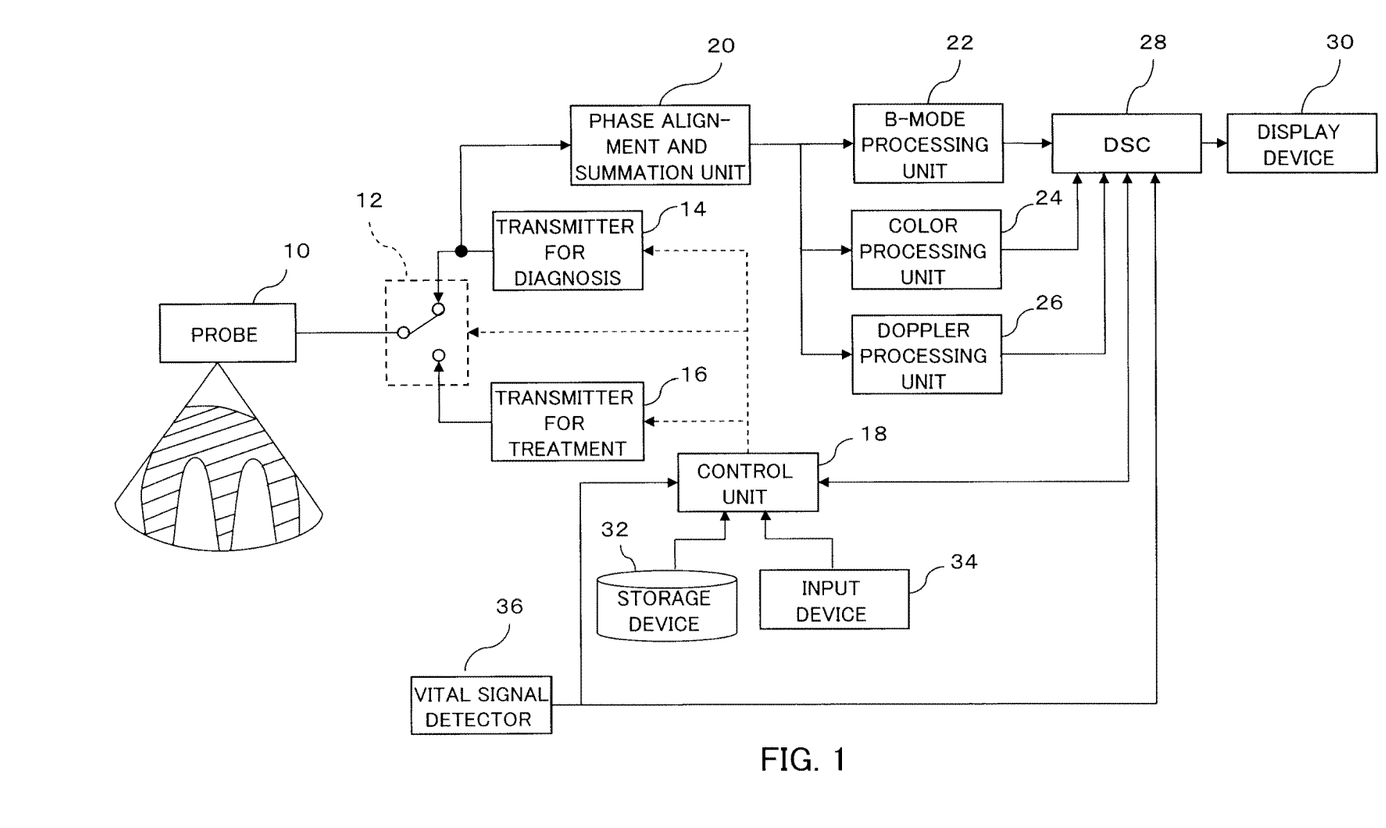
FIG. 1 View for schematically illustrating an example structure of an ultrasound treatment device according to an embodiment.

By reference to FIG. 1, a structure of an ultrasound treatment device according to an embodiment of the present invention will be schematically described. As illustrated in FIG. 1, an ultrasound treatment device includes a probe 10 for irradiating a living organism to be treated with ultrasound. This probe 10 is used for both treatment and diagnosis (observation within a living organism), and, in a preferable example, emits ultrasound for treatment and ultrasound for diagnosis from common transducers. The probe 10 preferably has a function of generating ultrasound pulse beams for forming a diagnostic image, and, further preferably, is capable of forming a two-dimensional tomographic image or generating volume data of a three-dimensional space by one-dimensionally or two-dimensionally scanning the beams. The scanning method of the ultrasound beam may be an electronic method, a mechanical method, or a combination thereof. For example, the probe 10 may include a one-dimensional electronic scanning type transducer array, such as a linear array or a sector array, or may include an electronic scanning type two-dimensional transducer array. In the latter case, it is possible to scan a three-dimensional space with an ultrasound beam. Further, the probe 10 may be a mechanical 3D probe which performs mechanical scanning with an electronic scanning type one-dimensional transducer array in a direction orthogonal to the transducer arrangement direction, thereby scanning a three-dimensional space with an ultrasound beam.

The probe 10 is connected, via a switch 12, to two transmitters, a transmitter for diagnosis 14 and a transmitter for treatment 16. The transmitter for diagnosis 14 generates a transmission signal for transducer driving used for diagnosis, which is used in a normal ultrasound diagnosis device. The transmitter for diagnosis 14 functions as a transmission beam former. Specifically, the transmitter for diagnosis 14 supplies a driving signal to each of transducers included in the transducer array of the probe 10, and applies appropriate phase delay to each driving signal in accordance with the beam direction, focus depth, and the like, to thereby generate an ultrasound beam pulse. Here, the center frequency of the ultrasound for diagnosis may be similar to that of normal ultrasound aimed at diagnosis (e.g., 1 to 2 MHz).

In contrast, the transmitter for treatment 16 generates a transmission signal with power for causing the transducer to generate ultrasound with intensity for treatment. For example, in the case of the use for treatment for promoting angiogenesis and vascular proliferation in an ischemic tissue such as myocardial infarction, it has been known that vascular proliferation within a tissue can be promoted even with low-pressure ultrasound with power which is only about two to three times as strong as the ultrasound beam for use in diagnosis, if such ultrasound irradiation is applied for a relatively long time period. Ultrasound with such a degree of power can be emitted from a conventional diagnosis ultrasound probe. For the reasons described above, in the present example, the probe 10 is used for both diagnosis and treatment (although this is not essential). Here, an example center frequency of the ultrasound for treatment is 2 to 5.5 MHz (e.g., 3.5 MHz).

In this example, the transmitter for treatment 16, similar to the transmitter for diagnosis 14, supplies a driving signal to each transducer for forming a transmission ultrasound beam. Similarly, the transmitter for treatment 16 may also control the phase difference of the driving signal to be supplied to each transducer so as to scan the ultrasound beam for treatment and vary the focus depth thereof.

When the probe 10 is a one-dimensional array, in both diagnosis and treatment, the probe 10 covers only a tomographic plane with electronic scanning. Therefore, when performing observation or treatment in a three-dimensional space, the one-dimensional array probe can be scanned in a direction that is different from the array direction (typically, a direction orthogonal to the array direction) automatically (e.g. a mechanical 3D probe) or manually (e.g., along a guide that restricts the movement of the probe).

The switch 12 selectively connects to the probe 10 an output of either the transmitter for diagnosis 14 or the transmitter for treatment 16.

When the transmitter for diagnosis 14 is selected by the switch 12, a driving signal for diagnosis is supplied from the transmitter for diagnosis 14 to the probe 10. This driving signal is converted into mechanical vibration by each of the transducers of the probe 10, and an ultrasound beam is to be transmitted. This ultrasound beam is reflected in the inner portion of a living organism which is an observation subject, and the reflected ultrasound (echo) is converted into an electrical signal by the transducers of the probe 10. The electrical signal (reception signal) generated by receiving echo by each transducer is input via the switch 12 to a phase alignment and summation unit 20. The phase alignment and summation unit 20 matches the phases of the reception signals of the transducers and adds the signals together to thereby form a signal corresponding to a reception beam.

A B-mode processing unit 22 executes detection, logarithmic compression processing, or the like, with respect to a signal after the phase alignment and summation, thereby forming a B-mode image. A color processing unit 24 forms a so-called color Doppler image which represents the motion speed of bloodstreams, tissues, or the like, in the beam direction, from the signal which has been subjected to the phase alignment and summation. For example, the color processing unit 24 executes quadrature detection processing by mixing a reference signal with respect to the signal which has been subjected to the phase alignment and summation by a quadrature detection circuit, and obtains a resultant complex signal. The color processing unit 24 then executes an autocorrelation operation with respect to the complex signal, and performs an arctangent operation with respect to a complex signal obtained as a result of the autocorrelation, thereby computing the speed which is a speed component along the ultrasound beam direction. A Doppler processing unit 26 obtains an image such as a spectral Doppler signal or the like, from the signal which has been subjected to the phase alignment and summation.

A DSC (digital scan converter) 28 converts (and interpolates, as required) each of the images (which are represented by a coordinate system of the beam scanning at this time point) input from the B-mode processing unit 22, the color processing unit 24, and the Doppler processing unit 26, into an image of a coordinate system of a display device 30, and combines the converted images to form a display image to be displayed on the display device 30. Here, while in the example of FIG. 1, there are provided the processing units that generate three types of images, the B-mode processing unit 22, the color processing unit 24, and the Doppler processing unit 26, this structure is not essential.

A control unit 18 is a unit that controls the ultrasound treatment device of the present embodiment as whole. In relation to the present embodiment, the control unit 18 controls a flow of treatment in which ultrasound is used. For example, the control unit 18 controls the switch 12 to control whether the probe 10 is used for either treatment or diagnosis (formation of an image within a living organism). The details of the control unit 18 will be described below.

A storage device 32 is a large capacity storage device such as a hard disk, for example, for storing an image and so on. In relation to the present embodiment, treatment record information including diagnostic images captured at respective inspection timings during the treatment is stored in the storage device 32.

An input device 34 is a device for entering instructions with respect to the ultrasound treatment device, and includes (at least one of) a key pad, a pointing device such as a mouse or trackball, or a touch panel, for example. In relation to the present embodiment, the input device 34 is used for designation of a treatment range.

A vital signal detector 36 detects a periodic vital phenomenon of a living organism to be treated and outputs a vital signal representing the vital phenomenon. The vital signal detector 36 may include an electrocardiograph. In this case, the signal representing the periodic vital phenomenon may include, for example, a characteristic waveform (e.g., R wave) periodically appearing in an electrocardiogram signal, for example. When the target portion to be treated is a heart, for example, with the use of a signal of an electrocardiogram, control which takes into consideration systolic time intervals can be performed in formation of a diagnostic image or the like. Further, it is also possible to use a respiration monitor as the vital signal detector 36 to control formation of a diagnostic image with reference to a periodical signal representing the start time point of exhalation or inspiration, and the like.

Figure 2:
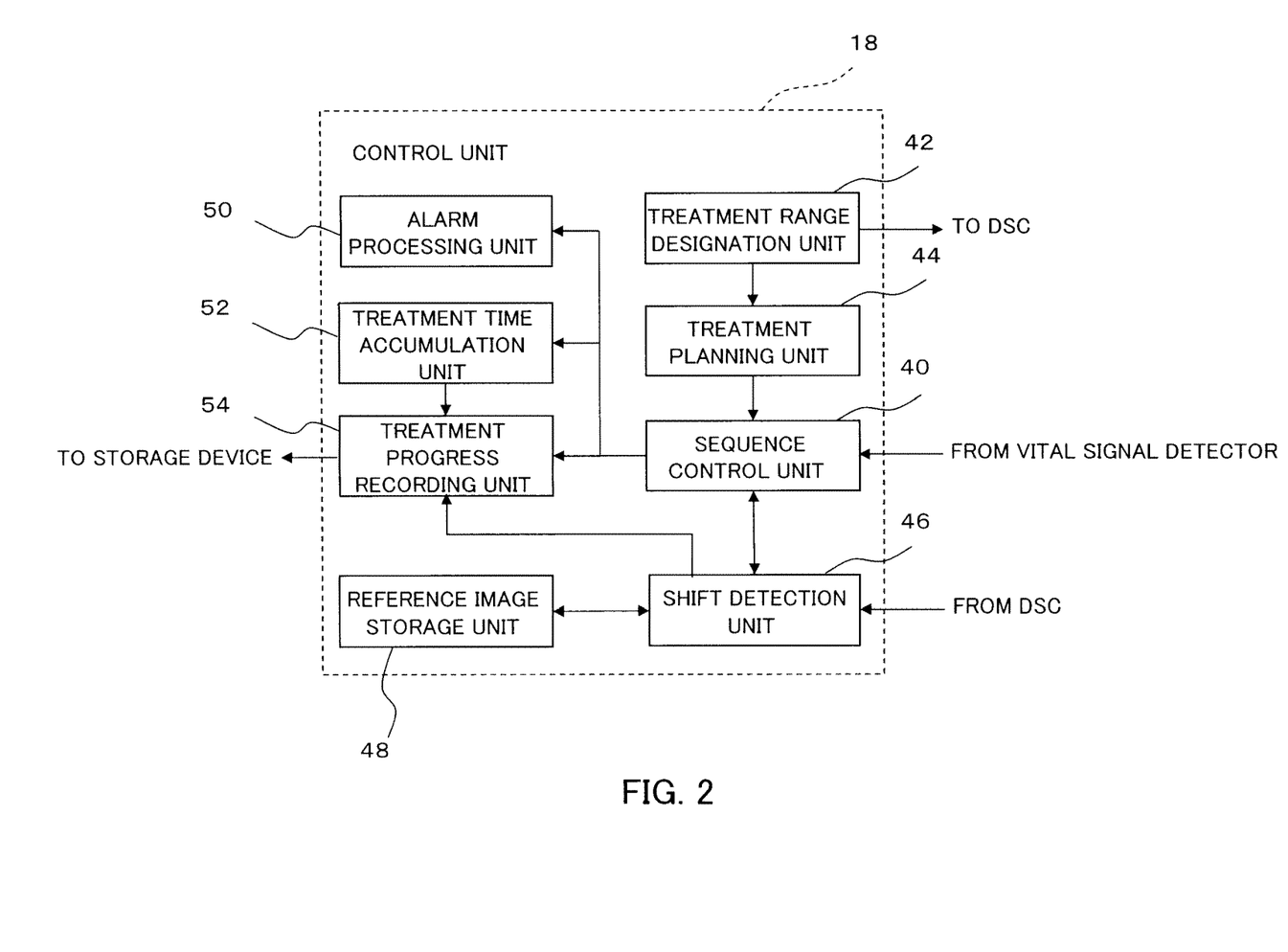
FIG. 2 View illustrating an example structure of an inside of a control unit.

Next, by reference to FIG. 2, the details of the control unit 18 will be described. FIG. 2 illustrates each of the functions used for control for treatment, among various functions of the control unit 18.

Among the functions of the control unit 18, a sequence control unit 40 performs management of a processing sequence of each of the units of the ultrasound treatment device at the time of ultrasound treatment.

Figure 3:
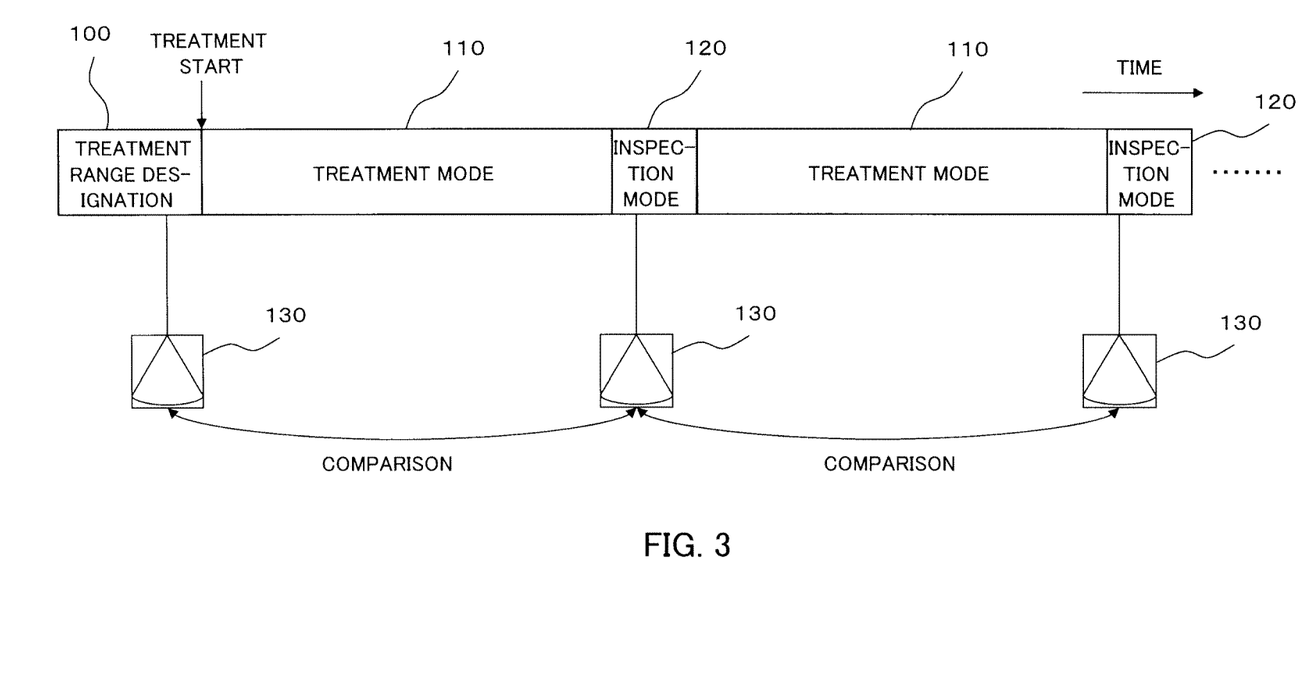
FIG. 3 View for explaining an example treatment sequence.

In an ultrasound treatment processing sequence of the present embodiment, as illustrated in FIG. 3, after treatment range designation 100, a treatment mode 110 for applying ultrasound irradiation with intensity for treatment and an inspection mode 120 for checking a positional shift of a treatment portion are alternately repeated. In the treatment mode 110, with the use of the transmitter for treatment 16, the ultrasound with intensity for treatment is emitted from the probe 10 toward the treatment portion for a predetermined unit time (e.g., about several seconds to several minutes: one minute, as an example). In the inspection mode 120, a diagnostic image 130 (e.g., a B-mode image) is formed by the transmission ultrasound from the transmitter for diagnosis 14, and is then compared with a past diagnostic image 130 (e.g., a diagnostic image formed in the previous shift inspection processing 120), thereby detecting a positional shift of the treatment portion displayed within the diagnostic image 130. As the time period required for the inspection mode 120, a sum of time for obtaining a diagnostic image corresponding to one frame and time for image comparison is sufficient, and therefore as long as one second suffices, which is much shorter than the unit time for the treatment mode 110. The unit time for the treatment mode 110 and the inspection mode 120 may be designated by a user or may be previously determined as default values.

The sequence control unit 40 controls each unit, including the switch 12, so as to realize such a processing sequence including the treatment range designation 100 and alternate execution of the treatment mode 110 and the inspection mode 120. The sequence control unit 40 further executes predetermined shift correction processing when a positional shift of the treatment portion is detected in the inspection mode 120. The shift correction processing includes, as an example, processing for interrupting the processing sequence in which the treatment mode 110 and the inspection mode 120 are alternately executed and prohibiting switching to the treatment mode 110 until resumption of treatment is instructed from the user (a doctor or the like). Further, as the shift correction processing, it is also possible to issue an alarm such as by sound or screen display (or both) to encourage the user to perform an operation for eliminating the positional shift of the treatment portion.

A treatment range designation unit 42 receives designation of the treatment range from the user. In this embodiment, a diagnostic image which is obtained when the probe 10 is driven with the transmitter for diagnosis 14 is displayed on the display device 30, and designation of the treatment range by the user is accepted on this diagnostic image. Specifically, the user confirms a portion to be treated on the diagnostic image, and enters the treatment range including a part or whole of the portion to be treated. For example, the treatment range can be designated as a range defined by a figure which is bounded by lines parallel to the beam direction and the scanning direction of the ultrasound beam (which is a rectangle in the case of linear scanning). In this case, the treatment range can be uniquely defined by operating the input device 34 (e.g., a trackball) to designate the positions of two points on diagonals of such a figure.

For example, FIG. 4(a) is an example case of ultrasound treatment with respect to myocardial infarction. In this example, in a diagnostic image range 152 having a sector shape of a sector scanning probe, a treatment range 154 which covers the angle range (the range in the electronic scanning direction) and the depth range (the range in the beam direction) of a part of the sector shape is set. This treatment range 154 has been set on a diagnostic image 130 schematically illustrated in FIG. 4(b), such that a significant part of the portion to be treated 132 which is identified by the user on the diagnostic image 130 is included. An image of the treatment range 154 may be formed and displayed so as to superpose the diagnostic image 130, as illustrated in FIG. 4(c). The treatment range 154 may be represented as a frame having a designated color (with the inside thereof being blank) or a plane having a translucent color, for example, and also may be represented by various other methods. An image of such a treatment range 154 can be supplied to the DSC 28 to superpose the diagnostic image 130. By superposing the treatment range 154 on the diagnostic image 130, it is possible for a user to visually recognize which portion within the living organism is irradiated with the treatment ultrasound. Accordingly, when the treatment portion has shifted from its original position due to a movement of a patient during the treatment, for example, the user can recognize that the treatment portion 132 lies outside of the treatment range 154, by observing the display device 30.

Figure 4:
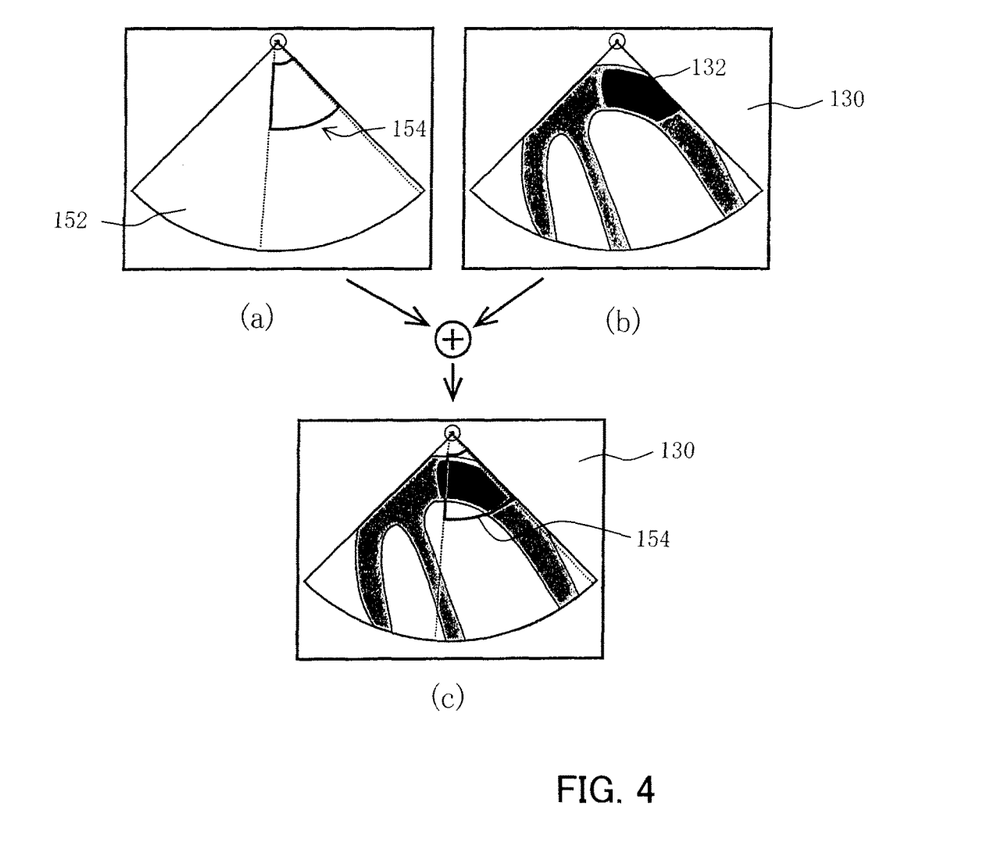
FIG. 4 View for explaining designation of a treatment range and example screen display of a treatment range.

While FIG. 4 illustrates an example of designation of a two-dimensional treatment range, the device of the present invention may be configured such that a three-dimensional treatment range can be designated in examples in which a 2D array or a mechanical 3D probe is used.

A treatment planning unit 44, based on the treatment range 154 which is designated and other parameters (e.g., the length of time for treatment) input by the user, creates a plan pattern for scanning of the ultrasound beam for treatment and moving of the beam focus. For example, the treatment planning unit 44 specifies, from the treatment range 154, the scanning range of the ultrasound beam for treatment and the variable range of the depth of the beam focus, and also specifies the scanning pattern and rate (scanning speed) of the ultrasound beam, and the pattern and rate of changing the focus depth. The sequence control unit 40 and the transmitter for treatment 16, in accordance with the treatment plan determined as described above, scan the ultrasound beam with intensity for treatment and vary the beam focus.

Further, the treatment planning unit 44 may receive designation of treatment time per unit area (irradiation time of ultrasound with treatment intensity) from the user and calculate the total treatment time concerning the whole treatment range 154 by, for example, multiplying the treatment time per unit area by the area of the treatment range 154. The total treatment time thus calculated can be used for the control of the treatment sequence by means of the sequence control unit 40. Further, the count number of irradiation of the ultrasound beam for treatment per unit area, in place of the treatment time per unit area, may be designated by the user, and in this case, control similar to that in the case of the treatment time can be performed. In the following description, a case in which the treatment time is designated by the user will be described as a representative example.

A shift detection unit 46, under the control of the sequence control unit 40, detects a positional shift of the treatment portion, by comparing the diagnostic image obtained in the inspection mode 120 with a past diagnostic image serving as a reference (which will hereinafter be referred to as a reference image). As the reference image, a diagnostic image obtained during the immediately previous inspection mode 120 may be used. Further, in another example, a fixed diagnostic image, such as the diagnostic image used for designation of the treatment range 154 or the diagnostic image obtained during the first inspection mode 120, may be used as the reference image. The reference image is obtained from the DSC 28 and stored in a reference image storage unit 48. The reference image storage unit 48 may be secured on a random access memory included in the sequence control unit 40. When the diagnostic image obtained during the immediately previous inspection mode 120 is used as the reference image, the reference image stored within the reference image storage unit 148 is rewritten for each inspection mode.

Figure 5:
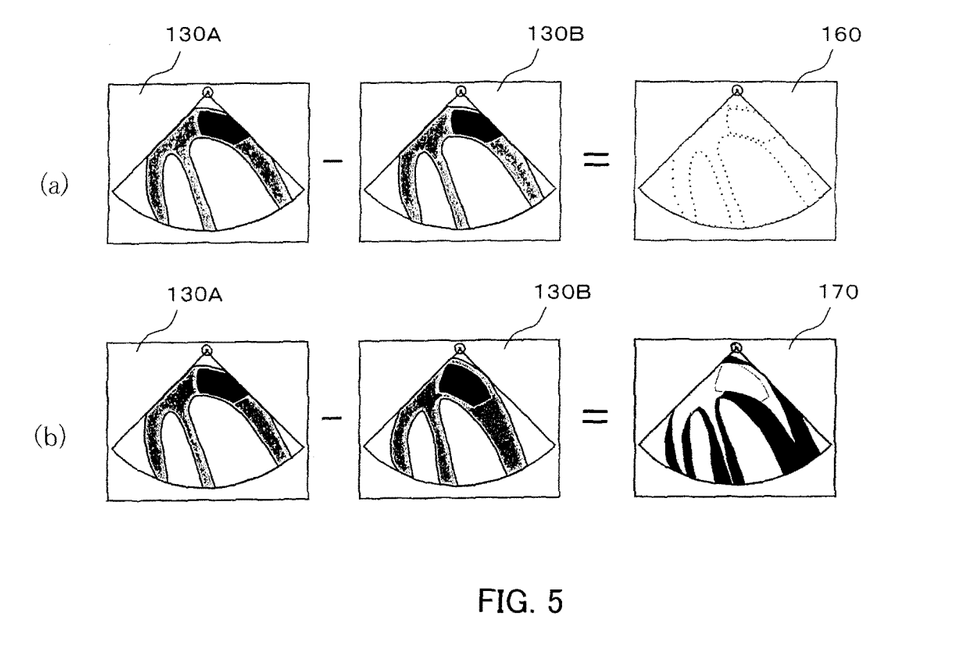
FIG. 5 View for explaining an example way of detecting a shift of a treatment target portion.

For the comparison between the current diagnostic image and the reference image in the shift detection unit 46, pixels of one image may be subtracted from the other image to form a difference image between these images. Then, whether or not a positional shift of the treatment portion has occurred may be determined based on the number of pixels having a pixel value other than 0 which are included in the difference image. For example, there may be performed processing in which it is determined that a positional shift has occurred when the number of pixels in the difference image having a pixel value other than 0 exceeds a predetermined value, and otherwise it is determined that no positional shift has occurred. Even when a pixel value is not exactly 0 in the difference image, determination of the pixel value being 0 may be made so long as the pixel value falls within an allowable range. In the example of FIG. 5(*a*), for example, as values of all the pixels of a difference image 160, which is a result of subtraction of the current diagnostic image 130B from the reference image 130A, are 0, it is determined that a positional shift has not occurred. In the example of FIG. 5(*b*), on the other hand, as a considerable number of pixels having pixel values other than 0 (indicated as black portion in the figure) are present in the difference image 170, it is determined that a positional shift has occurred.

The content of processing performed by the shift detection unit 46 described above is only an example. The shift detection unit 46 may employ any other processing, so long as the processing is operation processing which enables obtaining of a degree of difference between the two images, such as a correlation coefficient operation.

While the shift detection unit 46 which compares the whole reference image and the whole diagnostic image has been described above, this is not essential. Alternatively, the subject to be compared may be limited to a part of the image, such as an image within the treatment range 154.

When the subject is an organ which moves periodically by itself even if the posture of a patient is fixed, such as heart, the shift detection unit 46 compares diagnostic images captured at timings (time phases) when the organ is in the same motion state in the periodic motion pattern of the organ. For this purpose, a periodic vital signal output from the vital signal detector 36 is used. Specifically, the sequence control unit 40, based on a vital signal supplied from the vital signal detector 36, specifies a timing corresponding to a predetermined time phase, stores a diagnostic image frame at that timing as a reference image, and also, in every inspection mode 120, compares the diagnostic image at that time phase with the reference image. For example, images at a time phase which is a predetermined time after the R-wave of an electrocardiogram signal are compared with each other.

When a positional shift of the portion to be treated is detected, an alarm processing unit 50 informs the user of this fact by sound, screen display, or the like.

A treatment time accumulation unit 52 counts of the irradiation time of the ultrasound for treatment, starting from the time of starting the treatment. For example, the treatment time accumulation unit 52 accumulates the irradiation time in predetermined units, such as every one second, for example, during the treatment mode 110, and interrupts the accumulation during the inspection mode 120. When the accumulated time value by the treatment time accumulation unit 52 reaches a total treatment time which is previously determined by a treatment plan (or designation of a user), the sequence control unit 40 stops irradiation of the ultrasound for treatment to terminate the treatment sequence. Further, the accumulated time value of the treatment time accumulation unit 52 may be recorded as one item of the treatment progress record.

Here, the device may be configured to receive designation of the total treatment time itself from the user or, alternatively, may be configured to receive designation of the treatment time per unit area from the user and calculate the total treatment time based on the area of the treatment range 154 designated by the user. In the former case, when an identical total treatment time is designated for the treatment ranges with different areas, the treatment time per unit area varies among the treatment ranges, whereas in the latter case, as the total treatment time varies among different areas of the treatment ranges, it is possible to maintain the treatment time per unit area at the designated value.

A treatment progress recording unit 54 creates, for each period of the inspection mode 120, a treatment progress record including a diagnostic image obtained during that period and an accumulated value of the treatment time at the time point when the diagnostic image is generated, and stores the treatment progress record in a storage device 32. The treatment progress record may be recorded in association with other attribute information such as identification information of a patient, date and time information, and so on, for example. The treatment progress record as described above represents the effect and progress of the treatment with a set of the treatment (irradiation) time and the diagnostic image at the corresponding time, and therefore can be used, for example, as one piece of evidence of the treatment progress.

Each function of the control unit 18 has been described above. This control unit 18 can be implemented with a general purpose computer having a CPU (central processing unit) and a memory being used as a base. In this case, each of the functions described above is implemented by causing the CPU to execute a program describing the respective function described above. As a matter of course, a part or all of the functions may be implemented by a hardware circuit.

Next, with reference to FIGS. 6 and 7, an example processing procedure of the ultrasound treatment device according to the present embodiment will be described.

A user (doctor) sets the ultrasound treatment device to a diagnosis mode (inspection mode), and places the probe 10 on a patient to observe a diagnostic image of a vicinity of an affected area on the display device 30, moves the probe 10 to specify a portion to be treated, and positions the probe 10 at an optimum position (S10). The probe 10 is mounted on a mechanical holding mechanism, for example, and can be configured to maintain the located position by the holding mechanism. When the user designates a treatment mode in this state, the sequence control unit 40 causes a designation screen for the treatment range to be displayed on the display device 30, and accepts designation scanning of the treatment range by the user (S12). On the designation screen, an image (e.g. a B-mode motion image) within a living organism which is obtained by scanning of the ultrasound for diagnosis during the diagnosis mode is displayed, and the user specifies the treatment range in a manner as described above, while observing the image and operating the input device 34. At this time, in order to facilitate the range designation, the image display may be placed in a freeze (pause) state in accordance with the user's operation.

When the treatment range is designated, the treatment planning unit 44 creates a treatment plan corresponding to the treatment range as described above, and sets the treatment plan in the sequence control unit 40 and the transmitter for treatment 16 (S14). Thereafter, the sequence control unit 40 and the transmitter for treatment 16 are to execute the control in accordance with the plan.

When the creation and setting of the treatment plan is completed, a treatment sequence is to be started. The treatment sequence may be automatically started after the creation and setting of the treatment plan or may be started upon receiving a start command from the user.

Once the treatment sequence is started, among the diagnostic image frames obtained during the period of the treatment range designation, an image at a predetermined time phase or an image at a time phase designated by the user is stored, as a reference image (or a first reference image), in the reference image storage unit 48, and simultaneously a treatment progress record in the initial state is created by the treatment progress recording unit 54 and stored in the storage device 32 (S16). The treatment progress record in the initial state includes the diagnostic image at a predetermined time phase or a time phase designated by the user and information such as treatment (irradiation) time=0, for example.

Further, when the treatment sequence is started, the sequence control unit 40 resets the accumulated value of the treatment time accumulation unit 52 to 0 (seconds, for example; the time unit may be determined in accordance with the accuracy of time management which is required). The sequence control unit 40 further determines whether or not the accumulated value held by the treatment time accumulation unit 52 reaches the total treatment time which is designated (S18). When the accumulated value reaches the total treatment time, the treatment sequence is completed, and a screen indicating completion of the treatment, for example, is displayed. At the starting point of the treatment sequence, determination at step S18 would be negative (NO).

If the accumulated value does not reach the total treatment time, the sequence control unit 40 controls the switch 12 to select the transmitter for treatment 16, thereby shifting the ultrasound treatment device to the treatment mode and also causing the treatment time accumulation unit 52 to start count up of the time (S20). With this control, an ultrasound beam with intensity for treatment is emitted toward the treatment range within a living organism. The transmitter for treatment 16 temporally adjusts a driving signal to be supplied to each transducer of the probe 10 such that the beam position and direction and the focus depth change with time in accordance with the pattern of scanning and focus pattern indicated by the treatment plan.

Thereafter, the sequence control unit 40 continues the operation of the treatment mode 110 (i.e., irradiation of ultrasound with intensity for treatment and accumulation of the treatment time), from the starting time point of the current treatment mode 110, until the above-described unit time (e.g., about one minute), which is duration of one treatment mode 110, has elapsed (S22).

Here, during the period (unit time) of the treatment mode 110 described above, the display device 30 may display the reference image stored in the reference image storage unit 48. In this case, the image of the treatment range 154 may be superposed on the displayed image, so that the user can visually check which area is being treated, for example. At this time, a message or a mark indicating that the image being displayed is not a real-time image may be displayed, thereby reducing the possibility that the user misunderstands that the displayed image is a real-time image.

If it is detected, in step S22, that the unit time has elapsed from the start of the current treatment mode 110, the sequence control unit 40 switches selection of the switch 12 from the transmitter for treatment 16 to the transmitter for diagnosis 14, thereby shifting the ultrasound treatment device to the inspection (diagnosis) mode 20 (S24). At this time, the treatment time accumulation unit 52 is caused to stop the time accumulation. Consequently, the accumulated value held by the treatment time accumulation unit 52 remains at the current value until resumption of accumulation is instructed. In the inspection mode 120, an ultrasound pulse beam with intensity for diagnosis is transmitted from the probe 10 and a diagnostic image such as a B-mode image is generated from the echo and displayed on the display device 30. The diagnostic image may be displayed as a real-time motion image, or an image of the treatment range 154 may be superposed on the diagnostic image. With the image being displayed, the user can visually check the positional relationship between the treatment range and the treatment subject.

Further, the sequence control unit 40 instructs the shift detection unit 46 to perform detection processing of a positional shift of the treatment portion. The shift detection unit 46 compares an image (frame) at a predetermined time phase (the same time phase as the time phase of the reference image) which is determined based on a periodic vital signal from the vital signal detector 36, among the diagnostic images generated during the current detection mode 120, with the reference image stored in the reference image storage unit 48 to determine whether or not a significant shift (such as a shift exceeding the threshold value) has occurred (S26).

When it is determined that no significant shift has occurred in step S26 (i.e. the determination result in step S28 is negative), the sequence control unit 40 instructs the treatment progress recording unit 54 to record a treatment progress record (S16). The treatment progress recording unit 54 creates the treatment progress record, which includes the diagnostic image in the current inspection mode 120 which was used in the comparison in step S26 and the treatment time accumulated value indicated by the treatment time accumulation unit 52, and stores the treatment progress record in the storage device 32. At this time, in the case of setting in which the diagnostic image during the previous inspection mode 120 is used as the reference image for shift detection, the diagnostic image in the current inspection mode 120 which is used in the comparison in step S26 overwrites the diagnostic image obtained during the previous inspection mode as a new reference image in the reference image storage unit 48.

The sequence control unit 40 then determines whether or not the accumulated value held by the treatment time accumulation unit 52 has reached the designated total treatment time (S18), and if the designated total treatment time has not been reached, switches the ultrasound treatment device to the treatment mode 110 and allows the treatment time accumulation unit 52 to resume accumulation (S20). Thereafter, the processing in step S22 and the subsequent steps is repeated.

Figure 7:
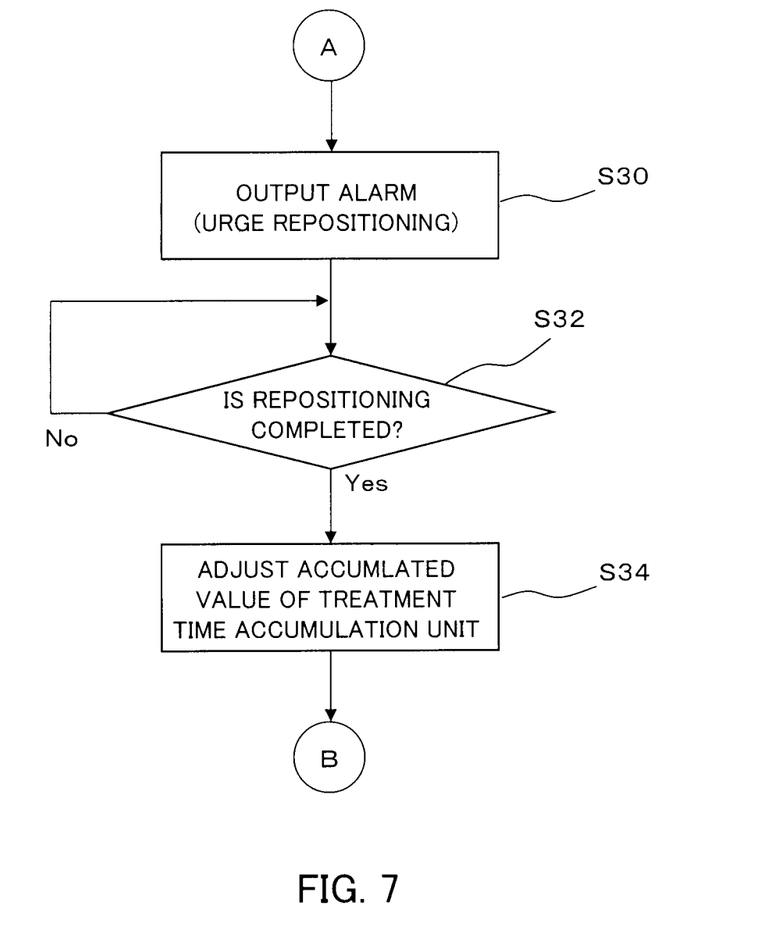
FIG. 7 View illustrating example processing performed when a shift of a treatment target portion is detected.

If it is determined that a significant shift has occurred in step S26 (the determination result in step S28 is affirmative), the processing proceeds to the procedure illustrated in FIG. 7. In this procedure, the sequence control unit 40 instructs the alarm processing unit 50 to execute alarm processing (S30). In the alarm processing, there is performed one or both of issuing an alarm sound and displaying a message or an image indicating occurrence of a positional shift of the treatment portion on the display device 30. Further, a message that urges the user to correct the positional shift may be displayed.

The user, in response to this alarm, adjusts the posture and position of the patient or the orientation and position of the probe 10 to reposition the probe 10 to the correct position and posture with respect to the portion to be treated (S32). In this reposition operation, the user adjusts the position and posture of the patient and the probe 10 while observing the diagnostic image displayed on the display device 30. During this period, a real-time diagnostic image, for example, is displayed on the display device, and the image of the treatment range 154 designated in step S12 is further superposed on the displayed image. Here, as the image of the treatment range 154 is fixed with respect to the position of the probe 10 on the screen, when the position or the posture of the patient or the probe 10 changes, a portion of the diagnostic image which falls within the treatment range 154 fixed on the screen, for example, also changes. Accordingly, the user adjusts the position or the posture of the patient or the probe 10 such that the portion to be treated correctly falls within the treatment range 154, while confirming the display. Here, as a guide for this reposition, the diagnostic image captured when the treatment range is determined in step S12 or the diagnostic image captured during the immediately previous inspection mode 120 (on which the treatment range 154 is superposed) may be juxtaposed with the real-time diagnostic image, so that the user can determine whether or not the repositioning is being correctly performed while comparing the guide image with the real-time diagnostic image. Further, at this time, it is also possible to cause the shift detection unit 46 to compare the diagnostic image captured at the time of repositioning (which should be at the same time phase as that of the reference image) with the reference image and to urge the shift detection unit 46 to perform further repositioning if there is a significant shift.

When the user, determining that repositioning has been correctly performed, instructs the ultrasound treatment device to resume the treatment, the sequence control unit 40 adjusts the accumulated value by subtracting the value corresponding to the time of the immediately previous treatment mode 110 from the accumulated value held by the treatment time accumulation unit 52 (S34). This processing is based on the view that because a positional shift has been detected in the inspection immediately after that treatment mode 110, it is assumed that the ultrasound for treatment was not emitted correctly in that treatment mode 110; i.e. that that treatment mode 110 itself was invalid. In this case, the whole time period of that treatment mode 110 which is assumed to be invalid is to be eliminated from the treatment (irradiation) time. To the contrary, there is another view that the time period of the treatment mode 110 immediately before the inspection in which the positional shift has been detected is also valid. Based on this view, the processing in step S34 is not necessary. The user may be allowed to set which view to select with respect to the ultrasound treatment device.

Figure 6:
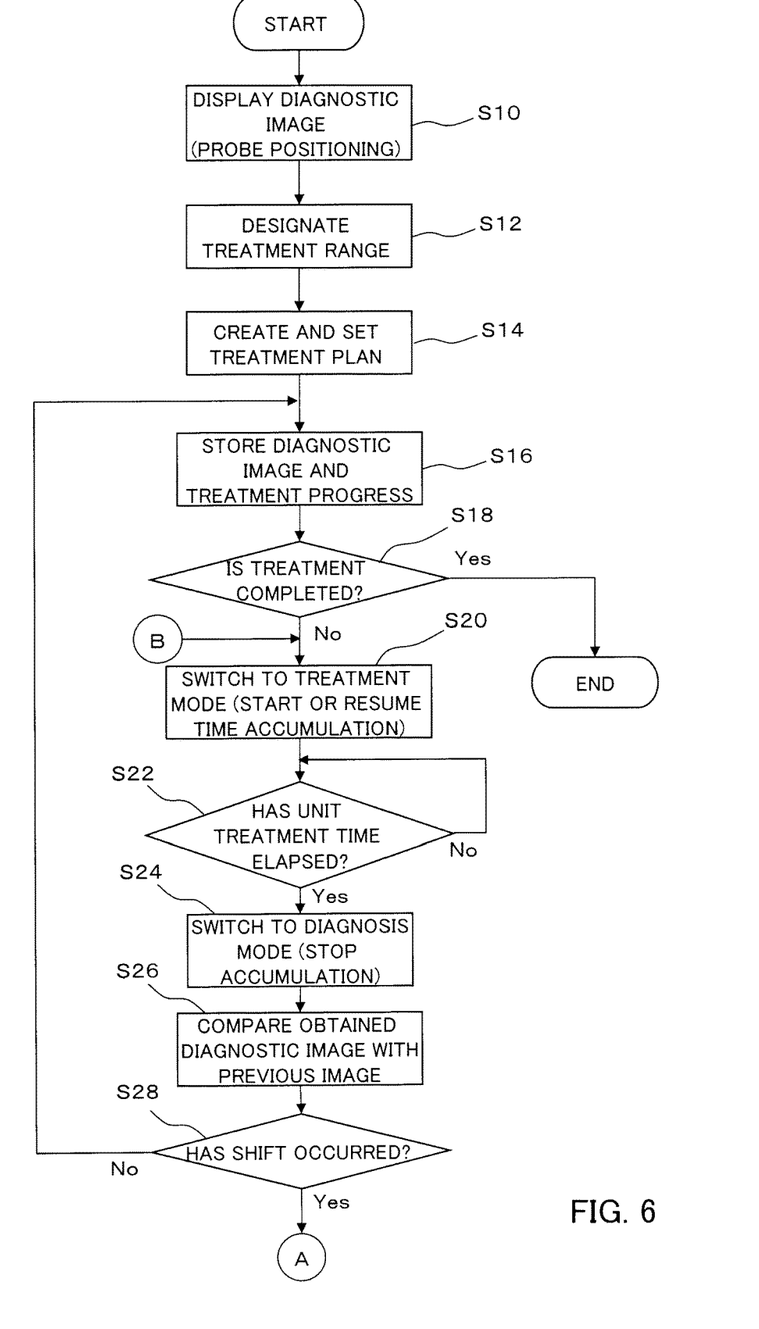
FIG. 6 Flowchart illustrating an example whole processing procedure according to the present embodiment.

When repositioning is performed and resumption of the treatment is instructed from the user as described above, the sequence control unit 40 returns the processing to the procedure in step S20 of FIG. 6 and proceeds to the processing by switching the ultrasound treatment device to the treatment mode 110.

Here, the procedure illustrated in FIGS. 6 and 7 is only an example, and various modifications may be made within the scope of the present invention.

In the above description, a typical example in which the probe 10 including a one-dimensional array is used to treat the treatment range within a tomographic plane covered by the array has been described. When the range to be actually treated has a three-dimensional expansion, on the other hand, the probe 10 may be shifted in a direction orthogonal to the array direction after completion of the treatment of a certain tomographic plane, for repeating the procedure illustrated in FIGS. 6 and 7. Further, there may be used a probe (mechanical 3D probe) including a mechanism that automatically controls a movement for gradually shifting the one-dimensional array in a direction which is orthogonal to the array direction. In this case, the treatment range in each of the tomographic planes at different shift positions in the direction orthogonal to the array direction may be common or may be designated separately for each tomographic plane. Also, a 2D array probe can be handled in a manner similar to the mechanical 3D probe. In the case of using a 2D array probe or a mechanical 3D probe, the device can be configured to enable designation of the treatment range on a three-dimensional volume image display.

As described above, according to the device of the present embodiment, a diagnostic image is formed periodically during irradiation of ultrasound with intensity for treatment, and then the diagnostic image is used to inspect whether or not a positional shift of the treatment portion has occurred. When, as a result of the inspection, a significant positional shift is detected, as control is performed such that irradiation of the ultrasound with intensity for treatment does not resume until the portion to be treated is correctly repositioned with respect to the irradiation range of the probe 10, it is possible to minimize application of irradiation of the ultrasound for treatment to a portion other than the treatment target portion.

Further, according to the present embodiment, as the single probe 10 is used for both diagnosis and treatment, a single origin of ultrasound and a single traveling route of ultrasound can be used for both forming a diagnostic image and treatment. It is therefore highly likely that irradiation of the ultrasound with intensity for treatment can be correctly applied to the treatment range 154 which is set by using a diagnostic image as a reference.

Here, while there might be considered a structure in which a generation source for ultrasound for treatment and a probe for diagnosis are provided as separate members and both members transmit ultrasound toward the same target portion from different locations on a body surface, with this structure, the ultrasound for treatment and the ultrasound for diagnosis travel along completely different routes in the body. The sonic velocity of ultrasound differs for different tissues due to the effects of differences in acoustic impedance between different tissues within a living organism, and even an identical length on a diagnostic image may mean different actual lengths within the living body, depending on the portions in accordance with the sonic velocity thereof. Accordingly, when the generation source for ultrasound for treatment and the probe for diagnosis are separate members, the likelihood that irradiation of the ultrasound for treatment is applied correctly to the treatment range which is indicated by the diagnostic image is lower than that in the case in which a single probe (i.e., the same transducer) is used for both diagnosis and treatment.

Figure 8:
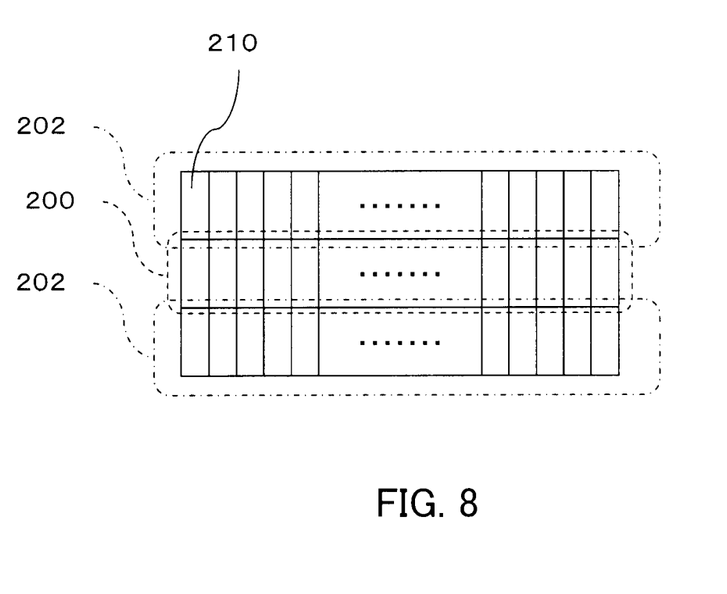
FIG. 8 View illustrating an example structure in which a transducer array for diagnosis and a transducer array for treatment are adjacently arranged.

Here, using exactly the same transducer array for both treatment and diagnosis is not necessarily essential. There may be used a probe, as illustrated in FIG. 8, in which a transducer array for diagnosis 200 and a transducer array for treatment 202, which are provided as separate arrays, are juxtaposed such that they are adjacent to each other in the direction orthogonal to the array direction. Even in this case, as the transducer array for diagnosis 200 and the transducer array for treatment are adjacent to each other, the origin of transmission of ultrasound and the propagation route of the ultrasound would be substantially the same for diagnosis and treatment. Here, while in the example illustrated in FIG. 8, a transducer 210 of the transducer array for diagnosis 200 and a transducer 210 of the transducer array for treatment 202 have the same size for the convenience of explanation, this is not essential. With the use of different transducers (transducer arrays) for diagnosis and treatment, the intensity of ultrasound for treatment can be made higher (than that when the same transducer is used for both purposes).

Further, according to the above embodiment, by using the transducer arrays for diagnosis and treatment located at substantially the same position (including the case of using the same transducer for both diagnosis and treatment), the control performed for applying irradiation of the ultrasound for treatment to the treatment range designated on the diagnostic image is facilitated. More specifically, by performing control of beam scanning and focus depth concerning the ultrasound for treatment similar to that for the ultrasound for diagnosis, it is possible to correctly irradiate the treatment range with the ultrasound for treatment.

Further, in the present embodiment, by defining the treatment range 154 as a range which is sectioned by lines parallel to the beam direction and the scanning direction, respectively, in a diagnostic image, it is possible to vary the line and focus depth of the beam for treatment within the treatment range merely by restricting the scanning range and the focus depth range in accordance with the treatment range. The shape of the treatment range as described above is merely an example. Even when the treatment range has an arbitrary shape, it is possible to control the beam scanning and the focus depth by the transmitter for treatment 16 in accordance with the shape.

Further, it is possible to provide an operation unit (e.g. a button) for switching between the treatment mode and the diagnosis (inspection) mode on the operation panel or the like of the ultrasound treatment device to thereby allow the user to perform mode switching as desired by the user during execution of the treatment sequence as described above (see FIG. 6). With this structure, when the user (a doctor or the like) recognizes a change of the patient's posture during execution of the treatment mode 110, for example, the user can operate the operation unit to forcedly switch to the inspection mode, thereby checking whether or not a positional shift of the treated portion has occurred.

Also, while in the above example, the inspection of a shift during the treatment is performed at periodic intervals (in other words, the length of all the treatment modes 110 is identical), this is not essential. The individual inspection timing may be determined based on other conditions, and may not necessarily be periodical.

In addition, while in the above example, the treatment for angiogenesis and revascularization of an ischemic tissue such as myocardial infarction has been described, the ultrasound treatment device according to the present embodiment may be applied to other treatment purposes.

REFERENCE SYMBOLS LIST

10 probe, 12 switch, 14 transmitter for diagnosis, 16 transmitter for treatment, 18 control unit, 20 phase-alignment and summation unit, 22 B-mode processing unit, 24 color processing unit, 26 Doppler processing unit, 28 DSC, 30 display device, 32 storage device, 34 input device, 36 vital signal detector.

The invention claimed is:

1. An ultrasound treatment device, comprising:
   a diagnosis ultrasound transmitter for transmitting ultrasound with intensity for diagnosis;
   a treatment ultrasound transmitter for transmitting ultrasound with intensity for treatment which is stronger than the intensity for diagnosis from a transmission position which is the same as a transmission position of the diagnosis ultrasound transmitter;
   a processor that causes the treatment ultrasound transmitter to transmit the ultrasound with intensity for treatment during a treatment period and also causes the diagnosis ultrasound transmitter to transmit the ultrasound with intensity for diagnosis at each inspection interval, thereby generating a diagnostic image at the inspection interval;
   the processor that detects a positional shift of a treatment target portion, based on comparison between a diagnostic image generated at a certain inspection interval and a diagnostic image which has been generated at an inspection interval prior to the certain inspection interval and stored;
   the processor that issues an alarm to a user when a positional shift of the treatment target portion is detected by the processor;
   the processor that, before the start of the treatment period in which the treatment ultrasound transmitter is used, causes the diagnosis ultrasound transmitter to transmit the ultrasound with intensity for diagnosis to thereby generate a diagnostic image for treatment range designation and display the diagnostic image that is generated on a display device; and
   the processor that receives from a user designation of a treatment range with respect to the diagnostic image for treatment range designation displayed on the display device,
   wherein the treatment period and the inspection interval are alternately repeated,
   wherein a time period for the inspection interval is a sum of time for obtaining the diagnostic image corresponding to one frame and time for image comparison,
   wherein an image of the treatment range is formed and displayed to be superposed on the diagnostic image, and
   wherein the treatment range is a range which is sectioned by lines parallel to a beam direction and a scanning direction, respectively, in the diagnostic image.
2. The ultrasound treatment device according to claim 1, further comprising:

the processor that controls the treatment ultrasound transmitter to transmit the ultrasound with intensity for treatment to the treatment range that is received by the processor.

3. The ultrasound treatment device according to claim 2, wherein the treatment ultrasound transmitter is capable of transmitting an ultrasound beam as the ultrasound with intensity for treatment, while varying a scanning position and a focus depth of the beam; and the processor causes the treatment ultrasound transmitter to transmit the ultrasound beam while varying the scanning position and the focus depth of the beam within the treatment range in accordance with a predetermined treatment plan pattern.

4. The ultrasound treatment device according to claim 1, further comprising:

the processor that counts an irradiation time duration in which the treatment ultrasound transmitter transmits the ultrasound with intensity for treatment from a start point which is a starting time point of the treatment period, wherein the processor, when a positional shift of the treatment target portion is detected by the processor, causes the processor to interrupt accumulation of the irradiation time duration until subsequent treatment by the treatment ultrasound transmitter is resumed, and when treatment by the treatment ultrasound transmitter is resumed subsequently, controls the processor to resume counting of the irradiation time duration from a value corresponding to a time point at which the positional shift was detected.

5. The ultrasound treatment device according to claim 2, further comprising:

the processor that counts an irradiation time duration in which the treatment ultrasound transmitter transmits the ultrasound with intensity for treatment from a start point which is a starting time point of the treatment period, wherein the processor, when a positional shift of the treatment target portion is detected by the processor, causes the processor to interrupt accumulation of the irradiation time duration until subsequent treatment by the treatment ultrasound transmitter is resumed, and when treatment by the treatment ultrasound transmitter is resumed subsequently, controls the processor to resume counting of the irradiation time duration from a value corresponding to a time point at which the positional shift was detected.

6. The ultrasound treatment device according to claim 3, further comprising:

the processor that counts irradiation time duration in which the treatment ultrasound transmitter transmits the ultrasound with intensity for treatment from a start point which is a starting time point of the treatment period, wherein the processor, when a positional shift of the treatment target portion is detected by the processor, causes the processor to interrupt accumulation of the irradiation time duration until subsequent treatment by the treatment ultrasound transmitter is resumed, and when treatment by the treatment ultrasound transmitter is resumed subsequently, controls the processor to resume counting of the irradiation time duration from a value corresponding to a time point at which the positional shift was detected.

7. The ultrasound treatment device according to claim 4, further comprising:

the processor that records, at each inspection interval, a diagnostic image generated at the inspection interval and a value of the irradiation time duration in the processor at the inspection interval.

8. The ultrasound treatment device according to claim 5, further comprising:

the processor that records, at each inspection interval, a diagnostic image generated at the inspection interval and a value of the irradiation time duration in the processor at the inspection interval.

9. The ultrasound treatment device according to claim 6, further comprising:

the processor that records, at each inspection interval, a diagnostic image generated at the inspection interval and a value of the irradiation time duration in the processor at the inspection interval.

10. The ultrasound treatment device according to claim 1, further comprising:

a vital signal detection unit that detects a vital signal corresponding to a periodical movement of a living organism to be treated, wherein the processor selects, as the inspection interval, a timing interval at which a time phase of a movement of the living organism which is obtained from the vital signal detected by the vital signal detection unit corresponds to a predetermined time phase.

11. The ultrasound treatment device according to claim 2, further comprising:

a vital signal detection unit that detects a vital signal corresponding to a periodical movement of a living organism to be treated, wherein the processor selects, as the inspection interval, a timing interval at which a time phase of a movement of the living organism which is obtained from the vital signal detected by the vital signal detection unit corresponds to a predetermined time phase.

12. The ultrasound treatment device according to claim 3, further comprising:

a vital signal detection unit that detects a vital signal corresponding to a periodical movement of a living organism to be treated, wherein the processor selects, as the inspection interval, a timing interval at which a time phase of a movement of the living organism which is obtained from the vital signal detected by the vital signal detection unit corresponds to a predetermined time phase.

13. The ultrasound treatment device according to claim 1, wherein the processor causes the treatment ultrasound transmitter to stop transmitting the ultrasound with intensity for treatment while a diagnostic image at the inspection interval is being generated by the diagnosis ultrasound transmitter.

14. The ultrasound treatment device according to claim 1, further comprising:

the processor that receives, when the ultrasound with intensity for treatment is being transmitted from the treatment ultrasound transmitter under the control of the processor, an instruction from the user to perform an operation to stop the transmission of the transmission ultrasound and cause the diagnosis ultrasound transmitter to transmit the ultrasound with intensity for diagnosis to thereby generate a diagnostic image.

15. A method for controlling an ultrasound treatment device comprising:
a diagnosis ultrasound transmitter for transmitting ultrasound with intensity for diagnosis; and
a treatment ultrasound transmitter for transmitting ultrasound with intensity for treatment which is stronger than the intensity for diagnosis,
the method comprising the steps of:
causing the treatment ultrasound transmitter to transmit the ultrasound with intensity for treatment from a predetermined transmission position during a treatment period;
causing the diagnosis ultrasound transmitter to transmit the ultrasound with intensity for diagnosis from a transmission position which is the same as the transmission position at each inspection interval, thereby generating a diagnostic image at the inspection interval;
detecting a positional shift of a treatment target portion, based on comparison between a diagnostic image generated at a certain inspection interval and a diagnostic image which has been generated at an inspection interval prior to the certain inspection interval and stored;
issuing an alarm to a user when a positional shift of the treatment target portion is detected;
causing, before the treatment period is started, the diagnosis ultrasound transmitter to transmit the ultrasound with intensity for diagnosis to generate a diagnostic image for treatment range designation and displaying the diagnostic image that is generated on a display device; and
receiving from a user designation of a treatment range with respect to the diagnostic image for treatment range designation displayed on the display device,
wherein the treatment period and the inspection interval are alternately repeated,
wherein a time period for the inspection interval is a sum of time for obtaining the diagnostic image corresponding to one frame and time for image comparison,
wherein an image of the treatment range is formed and displayed to be superposed on the diagnostic image, and
wherein the treatment range is a range which is sectioned by lines parallel to a beam direction and a scanning direction, respectively, in the diagnostic image.

16. The method for controlling an ultrasound treatment device according to claim 15, further comprising:
controlling the treatment ultrasound transmitter to transmit the ultrasound with intensity for treatment to the treatment range that is received.

17. The method for controlling an ultrasound treatment device according to claim 16, wherein
the treatment ultrasound transmitter is capable of transmitting an ultrasound beam as the ultrasound with intensity for treatment, while varying a scanning position and a focus depth of the beam; and
controlling the treatment ultrasound transmitter comprises causing the treatment ultrasound transmitter to transmit the ultrasound beam while varying the scanning position and the focus depth of the beam within the treatment range in accordance with a predetermined treatment plan pattern.

* * * * *